(12) United States Patent
Gilkerson et al.

(10) Patent No.: US 7,198,179 B2
(45) Date of Patent: Apr. 3, 2007

(54) SYSTEM FOR STORING AND DISPENSING A GAS-SOLUBILIZED PRODUCT

(75) Inventors: John S. Gilkerson, Cypress, CA (US); Jeffrey L. Creech, Marina Del Rey, CA (US); Li-Chien Hsu, Mission Viejo, CA (US); Gregory P. Watson, Laguna Niguel, CA (US)

(73) Assignee: TherOx, Inc., Irvine, CA (US)

( * ) Notice: Subject to any disclaimer, the term of this patent is extended or adjusted under 35 U.S.C. 154(b) by 526 days.

(21) Appl. No.: 10/374,220

(22) Filed: Feb. 25, 2003

(65) Prior Publication Data

US 2004/0166064 A1    Aug. 26, 2004

(51) Int. Cl.
   *B65D 83/00*    (2006.01)
(52) U.S. Cl. .................... 222/402.1; 222/105
(58) Field of Classification Search ............. 222/402.1, 222/105
   See application file for complete search history.

(56) References Cited

U.S. PATENT DOCUMENTS

| 3,819,092 | A | * | 6/1974 | Bonduris | 222/389 |
| 4,366,169 | A |   | 12/1982 | White | 424/285 |
| 4,470,520 | A | * | 9/1984 | Sullivan | 222/94 |
| 4,949,871 | A | * | 8/1990 | Flanner | 222/95 |
| 5,007,556 | A | * | 4/1991 | Lover | 222/386.5 |
| 5,277,336 | A | * | 1/1994 | Youel | 222/105 |
| RE35,540 | E |   | 6/1997 | Davies et al. | 222/402.1 |
| 5,834,519 | A |   | 11/1998 | Spears | 514/938 |
| 5,885,564 | A |   | 3/1999 | Zastrow et al. | 424/74 |
| 5,922,305 | A |   | 7/1999 | Spears | 424/43 |
| 5,958,377 | A |   | 9/1999 | Spears | 424/43 |
| 6,169,117 | B1 |  | 1/2001 | Spears | 514/937 |
| 6,197,279 | B1 |  | 3/2001 | Spears | 424/43 |
| 6,228,378 | B1 |  | 5/2001 | Takanabe et al. | 424/401 |
| 6,238,645 | B1 |  | 5/2001 | Spears | 424/43 |

OTHER PUBLICATIONS

Oxynoid et al. Application of fluorocarbon emulsions as components of cosmetic and medical ointments. Art. Cells, Blood Subs., and Immob. Biotech. 1994; 22(4), 1331-1336.
Li-Chien Hsu et al. U.S. Appl. No. 10/253,572, filed Sep. 24, 2002, entitled, "Perfluorocarbon emulsions with non-fluorinated surfactants."

* cited by examiner

*Primary Examiner*—Philippe Derakshani
(74) *Attorney, Agent, or Firm*—Margaret A. Kivinski (57) ABSTRACT

A packaged gas-solubilized product is described. The gas-solubilized product contains a first gas with a first pressure. The product is placed into a flexible inner container made of a gas-impermeable material. The inner container is hermetically disposed inside an outer container. A space formed between the inner and the outer containers is charged with a second gas with an initial charging pressure. The initial charging pressure is higher than the pressure of the first gas contained in the product. Additionally, a product dispenser in a fluid connection with the product contained in the internal container is included. The present invention also provides a method of packaging a gas-solubilized product to prevent a change in the concentration of the gas dissolved in the product during its storage and dispensing.

20 Claims, 4 Drawing Sheets

SYSTEM FOR STORING AND DISPENSING A GAS-SOLUBILIZED PRODUCT

FIELD OF THE INVENTION

The invention relates generally to the packaging of products containing dissolved gas for storing and dispensing. Specifically, the present invention relates to an assembly of rigid and flexible containers that maintain dissolved gas concentration in a product during its processing, storing and dispensing.

BACKGROUND OF THE INVENTION

Skin care and pharmaceutical compositions containing dissolved gases, such as oxygen and carbon dioxide, apart from ordinary propellants, have become the focus of great interest in recent years. For example, it has been suggested that topically applied oxygen-containing formulations may induce the growth of blood vessels and new skin, improve skin metabolism, impede skin aging, and protect skin from injurious environmental effects (Oxynoid, O. E. et al., *Art. Cells, Blood Subs., and Immob. Biotech.*, 1994, 22(4), 1331–1336). Similarly, topically applied carbon dioxide-containing cosmetic compositions are claimed to stimulate blood circulation, improve dull looking skin, and diminish dark circles under eyes and uneven skin tone (U.S. Pat. No. 6,228,378). Accordingly, a number of topical cosmetic and therapeutic compositions containing dissolved gases, in particular oxygen and carbon dioxide, have been developed.

For example, U.S. Pat. No. 4,366,169 describes the use of oxygen-containing fluorocarbons (FCs) in the treatment of ischemic wounds such as those resulting from burns, cuts, abrasions, and surgeries (U.S. Pat. No. 4,366,169). U.S. Pat. No. 5,885,564 teaches oxygen-containing FC emulsions that include digestive treatment products of cells of vegetable matter or yeasts. It is believed that the synergy between FCs and digestive treatments lead to a higher oxygen content in the emulsion. U.S. Pat. No. 6,228,378 describes a viscous cosmetic composition containing carbon dioxide gas.

Gas-containing products are typically hermetically packaged in pressurized containers to avoid the loss of the contained gas to the outside. Dispensing systems which use pressurized containers are well known. In such systems, the product to be dispensed is provided in the container and the container is charged to a starting pressure. When the dispensing valve is activated, a pressure differential between the internal pressure of the dispenser and the ambient pressure results in the dispensing of the product from the container (U.S. Pat. No. Re.35,540). However, as the product is dispensed from a conventional pressurized container, displaced liquid volume within the container is filled with expanding gas and the container pressure decreases proportionately in accordance with Boyle's Law. As a result, concentration of the gas in the product decreases in proportion to the overall pressure loss within the product container. Therefore, conventional pressurized containers fail to maintain gas concentration in the product that is subject to recurring dispensing. Because most conventional pressurized, or aerosol cans only use dissolved volatile gas as a propellant for product delivery, and not for therapeutic purposes, this limitation is generally not problematic. However, the maintenance of high pressure within the product container during dispensation would advantageously ensure a high level of dissolved gas in the product throughout its use.

Recently, U.S. Pat. No. 6,228,378 suggested packaging a composition containing carbon dioxide into a container of a dual structure comprising an outer container and an inner bag. In order to achieve a high concentration of the carbon dioxide gas in the cosmetic composition, the inner bag is made of a gas permeable material and carbon dioxide gas is used as a propellant. The patent teaches "aging" the cosmetic composition for one week at room temperature to allow the carbon dioxide gas to permeate through the inner bag into the cosmetic composition in order to obtain the desirable gas concentration level. The "aging" process can be shortened by heating.

This approach, however, is not practical in cosmetic and therapeutic applications. Typical cosmetic and therapeutic applications require frequent, e.g., daily, dispensing of the product. Accordingly, there would not be sufficient time between the applications to carry out the required "aging." Also, such a system makes maintaining constant gas concentration in the product difficult, if not impossible. The "aging" process as described appears to be based on simple diffusive transport of carbon dioxide across the permeable membrane. This process is very slow and fails to provide even approximate control over the carbon dioxide levels within the dispensed product. In order to achieve constant gas concentration in the product, a careful metering of the "aging time" and maintaining the product under constant ambient conditions between the applications is required, which is not always practical. Furthermore, because the gas concentration is such a scheme is proportional to the charging gas pressure external to the permeable bag, as product is dispensed both the gas pressure and product gas concentration will decrease.

Therefore, currently available methods for packaging products containing dissolved gases either fail to maintain the gas concentration in the product or suffer from technical disadvantages that make their utilization in cosmetic and therapeutic products impractical.

SUMMARY OF THE INVENTION

In view of the above-noted shortcomings of the prior art, it is an object of the present invention to provide a device for holding and dispensing a product having a gas dissolved in it without a decrease in the concentration of the dissolved gas in the product. It is also an object of the present invention to provide a simple, reliable, and inexpensive method of packaging a product having a gas dissolved in it to prevent a change in the concentration of the gas dissolved in the product during its storing and dispensing.

These and other objects are achieved in the present invention by utilizing a novel assembly for holding and dispensing a product having dissolved in it a first gas with a first pressure. The assembly comprises a sealed rigid outer container; a flexible inner container made of gas impermeable material and holding the product in which the gas is dissolved, and a product dispenser in a fluid connection with the product contained in the internal container. The inner container is hermetically disposed inside the outer container. A space formed between the inner and the outer containers is charged with a second gas with an initial charging pressure. The initial charging pressure is higher than the pressure of the first gas dissolved in the product.

Typically, the space between the inner and the outer containers is filled with the charging gas first. Then, the inner container is filled with the product containing the dissolved gas. As a result, the pressure of the charging gas increases as the inner container is filled with the product due to a decrease in the volume of the space between the inner and the outer containers. As the product is dispensed from the inner container, the pressure of the charging gas reduces, but it never drops below the first pressure of the first gas dissolved in the product. Therefore, the present invention allows the concentration of the gas dissolved in the product to be maintained during its dispensing.

Accordingly, in another aspect, the present invention provides a method of packaging a product having a gas dissolved in it to prevent a change in the concentration of the gas dissolved in the product during its storage and dispensing. The method comprises:
  (a) providing a product having dissolved in it a first gas with a first pressure;
  (b) providing an assembly for holding and dispensing the product containing the dissolved gas, the assembly comprising:
    a sealed rigid outer container;
    a flexible inner container made of gas impermeable material hermetically disposed inside the outer container, whereby a space is formed between the outer container and the inner container; and
    a product dispenser in a fluid connection with the product contained in the internal container;
  (c) charging the space between the outer and the inner containers with a second gas with an initial charging pressure, wherein the initial charging pressure is higher than the first pressure; and
  (d) filling the inner container with the product containing the dissolved gas.

The first gas and the second gas may be either the same or different. The product may be undersaturated, saturated, or oversaturated with the first gas.

The product containing the dissolved gas may be in a form selected from the group consisting of milk, cream, lotion, gel, paste, spray, and aerosol foam. In one embodiment, the product containing the dissolved gas comprises a fluorocarbon (FC) emulsion saturated with oxygen. The concentration of oxygen in the emulsion is preferably at least about 0.3 ml of oxygen at standard temperature and pressure (STP) per one ml of emulsion to achieve therapeutic and cosmetic benefits.

The present invention offers many economical and technical advantages over the conventional packaging and methods for storing and dispensing gas-containing products. Since the assembly of the present invention allows a frequent dispensing of the product without a change in the dissolved gas concentration or gas dissolution, each application of the product has a constant dissolved gas concentration. Also, because in the present invention the gas may be mixed into the product under controlled conditions before packaging, a gas-saturated product with a precise desirable concentration of the dissolved gas can be easily prepared. Finally, the disclosed method of packaging a product containing a dissolved gas is fast, simple, and inexpensive.

The packaged products containing dissolved gas of the present invention are well suited to be used in applications in which local delivery of gases, such as oxygen and carbon dioxide, to the skin are desirable. For example, cosmetic and therapeutic compositions containing dissolved oxygen or carbon dioxide may be packaged in accordance with the method of the present invention. The packaged cosmetic and therapeutic products of the present invention may be conveniently used by skilled skin care professional or medical personnel in the office or by a consumer at home.

The above-mentioned and other features of this invention and the manner of obtaining them will become more apparent, and will be best understood, by reference to the following description, taken in conjunction with the accompanying drawings. These drawings depict only a typical embodiment of the invention and do not therefore limit its scope.

DETAILED DESCRIPTION OF THE INVENTION

For the purposes of the present invention, the following terms are defined as follows:

A gas-solubilized product is any composition that has any gas dissolved in it. There are no particular limitations on the type of the composition that may be used as long as it has a gas dissolved in it. For example, a composition may be a solvent, a solution, an emulsion, a suspension, a gel, or any other desired liquid or semi-solid gas-solubilized product. If liquid, the composition may be aqueous or non-aqueous, such as hydrocarbon or other non-water-miscible liquid. Also, there is no limitation on the viscosity of the product. For example, it may be a low-viscosity solution or a viscous emulsion or gel.

A gas-saturated product is a product in which the dissolved gas is in a state of thermodynamic equilibrium with the equivalent partial pressure of the pure gas. A partial pressure of a gas is defined as the pressure exerted by one gas in a mixture of gases, such that the combined partial pressures of the component gases equals the total pressure of the mixture of gases. If only one gas is present, the partial pressure of the gas is the same as the total pressure of the gas. If a gas mixture is present, the partial pressure of a component gas is equal to the mole fraction of the component gas multiplied by the total pressure. Accordingly, a product that is undersaturated with a dissolved gas has the capacity to solubilize more gas when exposed to an equivalent partial pressure of the pure gas and a product that is oversaturated with gas has the tendency to release gas from solution.

Fluorocarbon is a fluorinated hydrocarbon in which at least one hydrogen atom is replaced by a fluorine atom.

Perfluorocarbon is a substantially fluorinated or completely fluorinated material which is generally, but not necessarily, a liquid at ambient temperature and pressure and which has a high solubility for gases, such as oxygen and carbon dioxide. "Substantially fluorinated" in this specification means that most of the hydrogen atoms of a compound have been replaced by fluorine atoms, such that further replacement does not substantially increase the gas solubility of the compound. It is believed that this level is reached when at least about 80–90% of the hydrogen atoms have been replaced by fluorine atoms (U.S. Pat. No. 4,569,784).

An emulsion is a system consisting of a liquid dispersed with or without an emulsifier in a second immiscible liquid in the form of stable (non-coalescing) droplets or microdroplets.

Continuous phase is the carrier phase of an emulsion, wherein the fluid elements are in continuous contact and not isolated from one another.

Discontinuous phase is the phase of an emulsion, wherein the fluid elements are discrete and isolated from one another, as in the form of droplets or microdroplets, or contained within micelles.

Thickening agent is a chemical agent having the property that, when added to a liquid mixture, increases its viscosity, or resistance to flow.

In its first aspect, this invention provides a packaged gas-solubilized product comprising a product having dissolved in it a first gas with a first pressure and an assembly for holding and dispensing the gas-solubilized product. The first gas may be any gas that is desired in an application. For example, in one embodiment, the first gas is oxygen and the product is a cosmetic or a therapeutic product. In another embodiment, the first gas is carbon dioxide and the product is a cosmetic product. The product may be undersaturated, saturated, or oversaturated with the gas. The product may be substantially in any form. For example, the product may be in a form selected from the group consisting of milk, cream, lotion, gel, paste, liquid, solution, spray, and aerosol foam.

Figure 1:
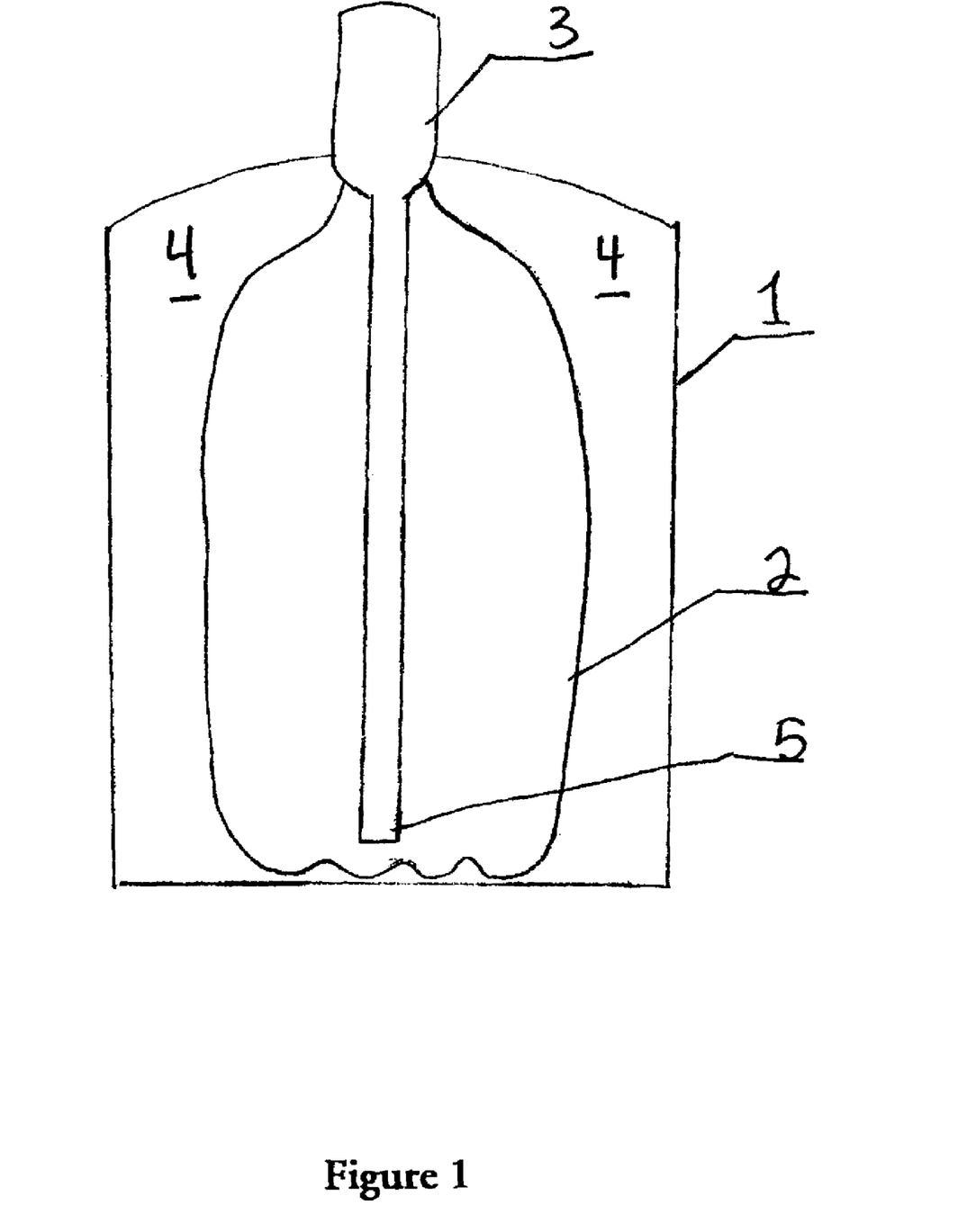
FIG. 1 schematically represents an assembly for holding and dispensing a gas-solubilized product in accordance with one embodiment of the present invention.

Referring to FIG. 1, the assembly comprises a sealed rigid outer container 1, a flexible inner container 2 made of gas-impermeable material and holding the gas-solubilized product, and a product dispenser 3 in fluid connection with the product contained in the inner container. The inner container 2 is hermetically disposed inside the outer container 1, whereby a space 4 is formed between the inner and the outer containers. The space 4 is charged with a second gas with an initial charging pressure. The initial charging pressure of the second gas is higher than the first pressure.

Figure 2:
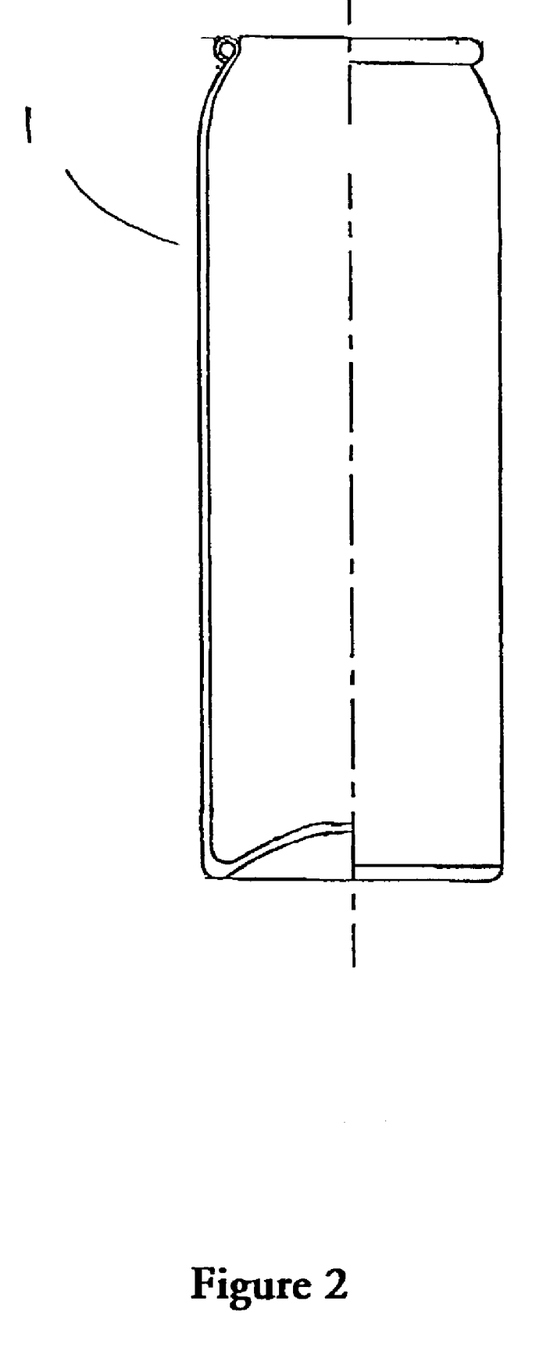
FIG. 2 schematically represents an outer container in accordance with one embodiment of the present invention with a partial cutaway view.

No particular limitation is imposed on the outer rigid container used in the present invention as long as it withstands the pressure of the second gas. For example, a metal container made of aluminum, stainless steel, steel or tin plate, a synthetic resin container made of an acetal resin or polycarbonate resin, laminated materials consisting of metals, plastics and coated papers, or a glass container may be used. Similarly, the inner flexible bag may be made of any flexible gas-impermeable material. For the purposes of the present invention, a material is flexible if it can be reversibly deformed without structural damage to the material. A material is gas-impermeable if it substantially prevents diffusion of the gas through the material. A preferred gas-impermeable material of the present invention has a gas permeability of 50 cc-mil/m$^2$-24 hr-atm or less. A suitable outer container 1 in accordance with one embodiment of the present invention is shown in FIG. 2.

Figure 3:
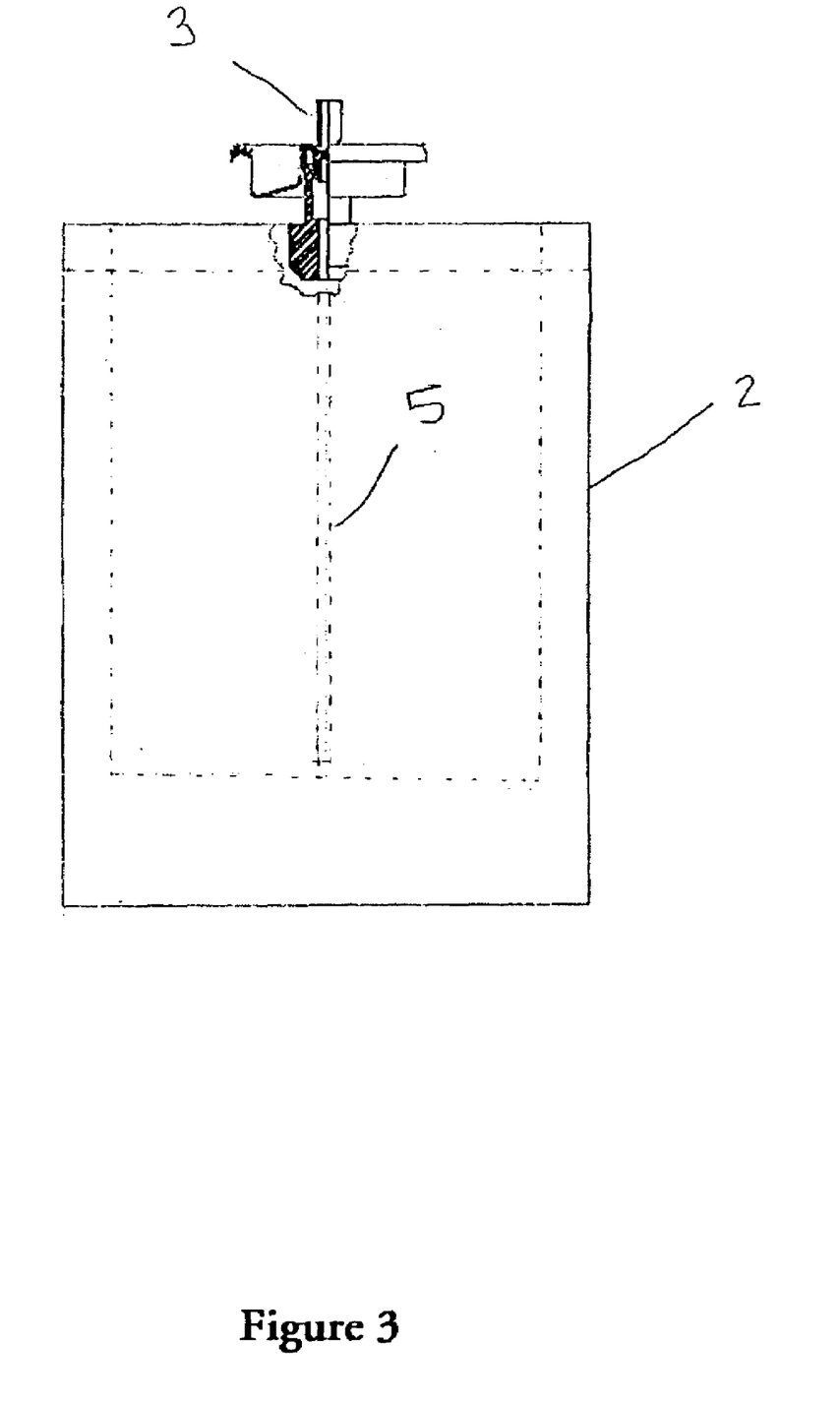
FIG. 3 schematically represents an inner container in accordance with one embodiment of the present invention in an unfolded position with an attached product dispensing means with a partial cutaway view thereof.

Referring to FIG. 3, examples of materials used for the inner container 2 are metal, foil, plastic films, coated or modified papers, and can include a single-layer structure or laminated structure. The material should be impermeable to the dissolved gas in the inner container 2 and the gas used to maintain the pressure in the space between the inner and outer containers, provide the required toughness and chemical resistance to the various contents of the packaging. The materials used in a laminated structure can be selected to impart desired properties to the inner container either alone or in combination. An example of a suitable laminated structure is a laminate of nylon, aluminum and polypropylene. In this embodiment the inner layer of the laminate, or the layer that is in direct contact with the product contained within the inner container 2, is polypropylene. In this embodiment polypropylene imparts chemical resistance to the product contained within the inner container 2. The middle layer of the laminate material in this embodiment is aluminum, which provides the requisite gas impermeability. The outer layer, which is in direct contact with the gas used to maintain the pressure within the outer container 1 is nylon which further provides toughness. An alternate embodiment of a laminated structure consists of an outer layer of cellophane, a second layer of polyethylene, a third layer of adhesive (e.g.,casein), and an innermost layer of polyethylene.

Different materials may also be used for different types of gases dissolved in the product or different gases used to maintain pressure within the outer container 1. For example, when the first gas is oxygen, the impermeable material may be selected from a group consisting of polymers and copolymers of nitriles, such as acrylonitrile-methacrylate copolymers, grafted nitrile rubbers, aluminum foil, polyvinylidene and chloride cellulose.

In one embodiment, the inner container 2 is folded along one edge to form a gusseted bottom and sealed along the other three edges as described in detail in U.S. Patent No. Re. 35,540, incorporated herein in its entirety by reference. As the inner container 2 fills with the product, it expands and the gusseted portion spreads along the bottom of the outer container 1. The gusset serves to prevent undue force on a seal between the product dispenser 3 and the inner container 2 when product is in the bag because the mass of the product rests on the bottom of the outer container 1 rather than being supported by the inner container/dispenser interface if the bag were to hang in free space. The gusset controls the fill operation so that the bag fills more evenly and more fully.

The product dispenser 3 may comprise a standard valve assembly for injecting the product into the internal container during manufacture and dispensing the product during consumer use. Alternatively, a wedge-shaped connector providing an enhanced connection point for the inner container and valve assembly may be used as described in U.S. Patent No. Re. 35,540. The valve can be made of one or more materials including nylon, 302 stainless steel, buna-N and glass-filled polypropylene. The valve may have an orifice of varying size depending on the desired product flow. A standard-type valve used with the assembly of the present invention causes the product to be exposed to shear created by the restricting orifice when filling and dispensing product from the inner container 2. Another valve that may be used has a one-way bypass feature which allows the product to flow around the restricting orifice when filling the inner container 2. There are several advantages associated with the use of this type of valve, including:

1. If the product is shear sensitive, it is only exposed to high shear passing through the restricting orifice one time, when it is dispensed from the container for use;
2. Smaller, more restrictive orifices can be used because filling time and shear are not factors. This is particularly advantageous for product handled at high pressure to provide more controlled dispensing.
3. The efficiency of the manufacturing process is improved because the time required to fill the container is reduced by having the product bypass the restricting orifice.

A flow device 5 may be used to promote product flow and increase evacuation percentages, especially for viscous products. The flow device 5 may extend substantially the full length of the inner container 2. Flexible containers pressurized from the outside begin to collapse around their center after about 60% of the product has been dispensed. With viscous materials or for light structure bags, this collapsing action can close the inner container 2, blocking the flow of product to the exit at the top of the dispenser. The flow device 5, positioned just below the inner container exit, will maintain flow for materials trapped in both the top and bottom of the inner container 2. The flow device 5 may take many shapes as described in U.S. Patent No. Re. 35,540. The flow device 5 allows the product in the bottom portion of the inner container 2 to make its way to the product dispenser 3 even when the inner container 2 has begun to collapse.

Figure 4:
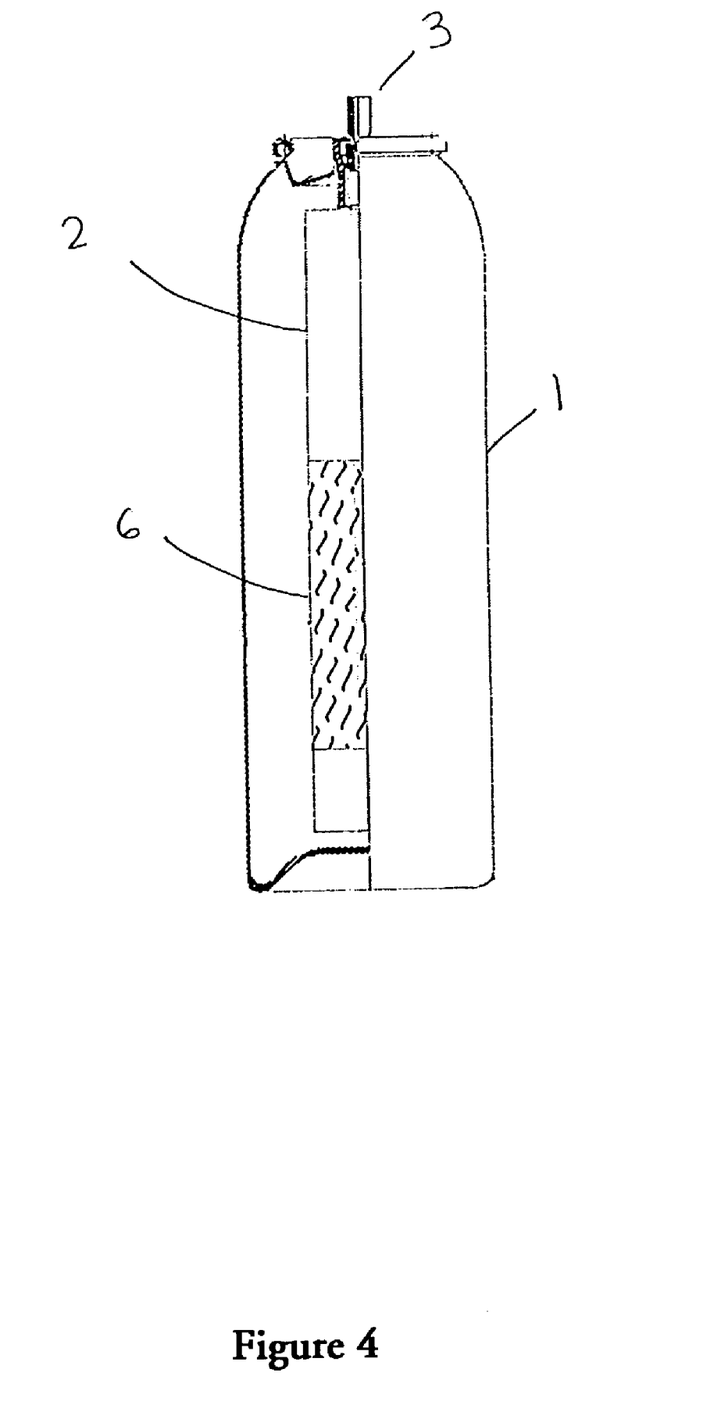
FIG. 4 schematically represents a complete assembly for holding and dispensing a gas-solubilized product in accordance with an alternate embodiment of the present invention.

The inner container 2 may be rolled into a tubular shape to ease its insertion into the outer container 1. Furthermore, as depicted in FIG. 4, a releasable restraint 6 may be used to maintain the inner container 2 in its collapsed rolled state until it is placed in the outer container 1 and the product is injected into the bag as described in U.S. Patent No. Re. 35,540.

The second gas that fills the space between the inner and the outer containers may be any gas that cannot penetrate the walls of the inner container 2. The second gas may be the same or different than the first gas contained in the product. Examples of the second gas include, but are not limited to, liquefied petroleum gas (LPG), dimethyl ether, nitrogen, carbon dioxide gas, oxygen, and any combinations thereof. Preferably, the second gas is an inert non-explosive gas such as nitrogen, carbon dioxide or one of the noble gases such as helium or argon. Preferably, the second gas serves as a non-contacting propellant for dispensing the product and allows full dispensation of the product (greater than 95% of the total charging weight dispensed).

The pressure of the second gas is not limited as long as the outside container 1 can withstand the pressure of the second gas after the inner container 2 is filled and as long as the charging pressure of the second gas is higher than the partial pressure of the dissolved first gas. In one embodiment, the first pressure is from about 15 to 250 psig, and the second pressure is from about 50 to about 300 psig. Other considerations that may affect pressure specifications are the product viscosity, desired dispensation force and container size, provided the pressure of the second gas remains higher than the partial pressure of the first gas.

In one embodiment, the gas-solubilized product comprises a fluorocarbon (FC) emulsion such as the one described in the co-pending patent application Ser. No. 10/253,572, incorporated herein in its entirety by the reference. Briefly, the FC emulsion comprises a continuous aqueous phase and a discontinuous phase comprising FC suspended as droplets within the continuous phase, wherein the FC emulsion further comprises an emulsifying agent and a stabilizing agent, wherein the stabilizing agent reduces the ability of the FC droplets to move within the continuous phase, and wherein the FC emulsion is loaded with oxygen.

Suitable FCs include, but are not limited to, linear, branched and cyclic fluorinated hydrocarbon compounds, derivatives and mixtures thereof FC may be a perfluorinated fluorocarbon (PFC). Examples of acceptable PFCs include, but are not limited to, C6–C9 perfluoroalkanes, perfluoroperhydrofluoranthrene, perfluorodecalin, perfluoroperhydrophenanthrene, bis(perfluor-hexyl)-1,2-ethene, perfluoro-1,3-dimethylcyclohexane, perfluoromethyldecalin, perfluoroisopropyldecalin, a mixture of perfluorodixylylmethane and perfluorodixylylethane, and a mixture of perfluoroperhydrophenanthrene and perfluoro n-butyl decalin. The FC emulsion may contain FCs in the amount from about 2% to about 90% (wt/wt), preferably from about 10% to about 70% (wt/wt). However, FC concentrations outside of the above ranges may also be used.

Any emulsifying agents capable of dispersing FC may be used. However, due to environmental concerns, preferably, the emulsifying agent is a non-fluorinated compound. Examples of such biocompatible, non-fluorinated compounds include, but are not limited to, a block copolymer of ethylene oxide and propylene oxide, phospholipids, and a polyoxyethylene derivative of a fatty acid ester of sorbitan. In one embodiment, a hydrogenated phospholipid is used. The hydrogenated phospholipid may be selected from the group consisting of hydrogenated phosphatidylcholine, lysophosphatidylcholine, phosphatidylethanolamine, phosphatidylserine, phosphatidylinositol, phosphanolipids, phosphatidic acid, and mixtures thereof. In a preferred embodiment, the hydrogenated phospholipid is hydrogenated phosphatidylcholine. Typically, the emulsifying agent is used in an amount in the range from about 1% to about 15% (wt/wt).

The stabilizing agent is a compound that reduces the ability of the FC droplets to move within the continuous phase. The stabilizing agent may be selected from the group consisting of cetyl alcohol, stearyl alcohol, behenyl alcohol, glyceryl stearate, polyoxyethylated fatty acid (PEG-75 stearate), polyethylene glycol ether of cetyl alcohol (ceteth-20), polyethylene glycol ether of stearyl alcohol (steareth-20), hydrogenated phosphotidylcholine, and mixtures thereof. Typically, the amount of the stabilizing agent is in the range from about 0.05% to about 20% (wt/wt). Preferably, the amount of the stabilizing agent is in the range from about 0.5% to about 5% (wt/wt). In one embodiment, hydrogenated phosphotidyl choline is used as both the stabilizing agent and the emulsifying agent.

In one embodiment, the gas-solubilized product is a cosmetic product comprising an oxygenated FC emulsion and cosmetic additives. Depending on the type of the intended use of the cosmetic composition of the present invention, the cosmetic additive may be selected from the group consisting of fatty substances, solvents, silicones, softeners, thickeners, anti-foaming agents, moisturizing agents, nutritive agents, vitamins, mineral salts, buffers, humectants, fillers, sequestering agents, surfactants, polymers, propellants, preservatives, colorants, buffers, texture enhancing compounds, sunscreens, antioxidants, free radical scavengers, chelating agents, fragrances, flavorings, and processing aids.

In another embodiment, the gas-solubilized product is a therapeutic product comprising an oxygenated FC emulsion. The oxygenated therapeutic composition of the present invention is well suited for use as either a prescribed pharmaceutical product or an over-the-counter (OTC) product. Accordingly, it may further contain pharmaceutically active ingredients. For the purposes of the present invention, an ingredient is pharmaceutically active if, when applied to an open wound or to the skin, it produces a detectable biological effect. Such pharmaceutically active ingredients are well known to those skilled in the art. For example, they may be selected from the group consisting of antibacterials, antihistaminics, anti-inflammatories, miotics, mydriatics, antiglaucomals, antivirals, carbonic anhydrase inhibitors, antifungals, anesthetics, immunosuppressive agents, vitamins, nutrients, and mixtures thereof.

A cosmetic or a therapeutic composition of the present invention may be loaded with oxygen by treating it in such a way that it becomes saturated with oxygen and carries more oxygen than it would without the treatment. Typically, the concentration of oxygen in the cosmetic or therapeutic composition of the present invention is at least about 0.3 ml of oxygen at standard temperature and pressure (STP) per one ml of FC emulsion at 1 atmosphere.

The cosmetic or therapeutic composition of the present invention may be supersaturated with oxygen. For example, in one embodiment, the concentration of oxygen in the cosmetic or therapeutic composition is at least about 1 ml of oxygen (STP) per 1 ml of FC emulsion. In another embodiment, the concentration of oxygen in the cosmetic or therapeutic composition is at least about 2 ml of oxygen (STP) per ml of FC emulsion. Usually, the equivalent partial pressure of dissolved oxygen in the cosmetic or therapeutic composition is at least about 760 mm Hg, and for the examples above, is substantially over 760 mm Hg.

In a typical embodiment, first, the space between the inner and the outer containers is charged with the second gas and sealed. Then, the inner container 2 is filled with the gas-solubilized product and the assembly is sealed. The pressure of the second gas increases as the inner container is filled with the product due to decrease in the trapped volume between the inner and the outer container. As the product is dispensed from the inner container 2 and is forcibly ejected from the can, the pressure of the second gas steadily reduces towards the limiting internal pressure that was applied before product was introduced into the inner container 2, such that the pressure of the second gas never falls below the equivalent partial pressure of the gas dissolved in the product. Therefore, the present invention allows the concentration of the gas dissolved in the product to remain constant during dispensation.

Accordingly, in another aspect, the present invention provides a method of packaging a gas-solubilized product to prevent a change in the concentration of the gas dissolved in the product during its storage and dispensation. The method comprises:

(a) providing a product having dissolved in it a first gas with a first pressure;
(b) providing an assembly for holding and dispensing the gas-solubilized product, the assembly comprising:
  a sealed rigid outer container;
  a flexible inner container made of gas-impermeable material hermetically disposed inside the outer container, whereby a space is formed between the outer container and the inner container; and
  a product dispenser in a fluid connection with the product contained in the internal container;
(c) charging the space between the outer and the inner containers with a second gas with an initial charging pressure, wherein the initial charging pressure is higher than the first pressure; and
(d) filling the inner container with the gas-solubilized product.

What is claimed is:

1. A packaged gas-solubilized product comprising:
(a) a product having dissolved in it a first gas with a first pressure, wherein the first gas has a concentration of at least about 0.3 ml at standard temperature and pressure per one ml product at 1 atmosphere; and
(b) an assembly capable of holding and dispensing the gas-solubilized product while maintaining the concentration of the first gas substantially the same during the holding and dispensing of the product, the assembly comprising:
  a sealed rigid outer container;
  a flexible inner container made of gas-impermeable material and holding the gas-solubilized product, wherein the gas-impermeable material has a gas permeability of 50 cc-mil/m$^2$-24 hr-atm or less, the inner container hermetically disposed inside the outer container, whereby a space is formed between the inner and the outer containers, wherein the space is charged with a second gas with an initial charging pressure, wherein the initial charging pressure is higher than the first pressure; and
  a product dispenser in a fluid connection with the product contained in the internal container.

2. The packaged gas-solubilized product of claim 1, wherein the outer container is made of a material selected from the group consisting of metal, plastic, glass and laminates thereof.

3. The packaged gas-solubilized product of claim 1, wherein the inner container is made of a material selected from the group consisting of flexible plastic, metal, paper and laminates thereof.

4. The packaged gas-solubilized product of claim 1, wherein the inner container has a gusseted bottom, wherein the bottom of the internal container rests against a bottom of an internal cavity of the outer container.

5. The packaged gas-solubilized product of claim 1, wherein the dispenser further comprises a valve assembly for injecting the product into the internal container and dispensing the product.

6. The packaged gas-solubilized product of claim 1, wherein the second gas serves as a non-contacting propellant for dispensing the product.

7. The packaged gas-solubilized product of claim 1, wherein a flow device serves as the fluid connection between the product dispenser and the product contained in the internal container.

8. The packaged gas-solubilized product of claim 1, wherein the first gas and the second gas are the same.

9. The packaged gas-solubilized product of claim 1, wherein the first gas and the second gas are different.

10. The packaged gas-solubilized product of claim 1, wherein the first gas is oxygen.

11. The packaged gas-solubilized product of claim 1, wherein the product is saturated or oversaturated with the first gas.

12. The packaged gas-solubilized product of claim 1, wherein the gas-solubilized product comprises a fluorocarbon (FC) emulsion.

13. The packaged gas-solubilized product of claim 11, wherein the FC emulsion comprises a continuous aqueous phase and a discontinuous phase comprising FC suspended as droplets within the continuous phase, wherein the FC emulsion further comprises an emulsifying agent and a stabilizing agent, wherein the stabilizing agent reduces the ability of the FC droplets to move within the continuous phase.

14. The packaged gas-solubilized product of claim 13, wherein both the stabilizing agent and the emulsifying agent are a hydrogenated phospholipid.

15. The packaged gas-solubilized product of claim 1, wherein the gas-solubilized product is a cosmetic or therapeutic product comprising a fluorocarbon (FC) emulsion and wherein the first gas is oxygen.

16. The packaged gas-solubilized product of claim 15, wherein the concentration of oxygen in the emulsion is at least about 0.3 ml of oxygen (STP) per one ml of FC emulsion.

17. The packaged gas-solubilized product of claim 15, wherein the equivalent partial pressure of dissolved oxygen in the product is at least about 760 mm Hg.

18. The packaged gas-solubilized product of claim 15, wherein the product is in a form selected from the group consisting of milk, cream, lotion, gel, paste, spray, and aerosol foam.

19. A method of packaging a gas-solubilized product to prevent a change in the concentration of the gas dissolved in the product during its storage and dispensing, the method comprises:

(a) providing a product having dissolved in it a first gas with a first pressure, wherein the gas has a concentration of at least about 0.3 ml at standard temperature and pressure per one ml product at 1 atmosphere;

(b) providing an assembly capable of holding and dispensing the gas-solubilized product while maintaining the concentration of the first gas substantially the same during the holding and dispensing of the product, the assembly comprising:

a sealed rigid outer container;

a flexible inner container made of gas-impermeable material hermetically disposed inside the outer container, wherein the gas-impermeable material has a gas permeability of 50 cc-mil/m$^2$-24 hr-atm or less, whereby a space is formed between the outer container and the inner container; and a product dispenser in a fluid connection with the product contained in the internal container;

(c) charging the space between the outer and the inner containers with a second gas with an initial charging pressure, wherein the initial charging pressure is higher than the first pressure; and (d) filling the inner container with the gas-solubilized product.

20. The method of claim 19, wherein the product is a cosmetic or therapeutic product comprising a fluorocarbon (FC) emulsion and wherein the first gas is oxygen.

* * * * *